United States Patent
Zeller (10) Patent No.: US 11,879,954 B2
(45) Date of Patent: Jan. 23, 2024

(54) CORRECTING THE CHEMICAL SHIFT ARTIFACTS FROM BIPOLAR DIXON MR ACQUISITION DATA

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 17/851,317

(22) Filed: Jun. 28, 2022

(65) Prior Publication Data
US 2022/0413077 A1 Dec. 29, 2022

(30) Foreign Application Priority Data
Jun. 29, 2021 (EP) .................................. 21182276

(51) Int. Cl.
*G01R 33/565* (2006.01)
*A61B 5/055* (2006.01)
(Continued)

(52) U.S. Cl.
CPC ........ *G01R 33/56527* (2013.01); *A61B 5/055* (2013.01); *G01R 33/4828* (2013.01); *G01R 33/5608* (2013.01)

(58) Field of Classification Search
None
See application file for complete search history.

(56) References Cited

U.S. PATENT DOCUMENTS 11,547,368 B2 * 1/2023 Zeller ................... G16H 30/40
11,580,626 B1 * 2/2023 Weiss ........................ G06T 7/90
(Continued)

FOREIGN PATENT DOCUMENTS

DE  102008057294 A1  5/2010
EP      3796023 A1  3/2021

OTHER PUBLICATIONS

Ronneberger, Olaf et al. "U-Net: Convolutional Networks for Biomedical Image Segmentation", http://lmb.informatik.uni-freiburg.de/Publications/2015/RFB15a.; 2015.
(Continued)

*Primary Examiner* — Rodney E Fuller
(74) *Attorney, Agent, or Firm* — Banner & Witcoff Ltd.

(57) ABSTRACT

In a method for correcting chemical shift artifacts, CSA, a convolutional neural network (CNN) may be provided, which is trained using acquisition data acquired in phase and in opposed phase by a DIXON MR method that may include acquisition data that contains CSA in mutually opposite directions and acquisition data that contains CSA only in one direction. The CNN may be trained to transform acquisition data obtained by the fast DIXON MR method so the acquisition data acquired by the fast DIXON MR method exhibits CSA that arise only in the same direction. The method may further include acquiring fast DIXON MR acquisition data using respective control instructions and applying the trained CNN to the acquisition data to minimize or entirely remove the CSA and to calculate corrected acquisition data. The CSA may arise in the magnetic resonance DIXON method when using fast DIXON MR to capture the echoes.

15 Claims, 5 Drawing Sheets

(51) Int. Cl.
 *G01R 33/48* (2006.01)
 *G01R 33/56* (2006.01)

(56) References Cited

U.S. PATENT DOCUMENTS

| 2010/0123460 | A1 | 5/2010 | Hughes et al. | |
|---|---|---|---|---|
| 2021/0080530 | A1 | 3/2021 | Zeller | |
| 2023/0184858 | A1* | 6/2023 | Nickel | G01R 33/5608 324/309 |

OTHER PUBLICATIONS

Leinhard et al:"Water fat shift displacement artifact correction in two point Dixon imaging", Proc. Intl. Soc. Mag. Reson. Med 16 (2008).

Ghodatri V. et al.: "MR image reconstruction using deep learning: evaluation of network structure and loss functions", Quant Imaging Med Surg 2019;9(9):1516-1527, https://www.ncbi.nlm.nih.gov/pmc/articles/PMC6785508/pdf/qims-09-09-1516.pdf.

Wikipedia "U-Net" https://en.wikipedia.org/wiki/U-Net (downloaded Nov. 13, 2020).

Ramzi Z.: "Benchmarking MRI Reconstruction Neural Networks on Large Public Datasets",Appl. Sci. 2020, 10, 1816; https://www.mdpi.com/2076-3417/10/5/1816/pdf.

Ma, Jingfei. "Dixon techniques for water and fat imaging." Journal of Magnetic Resonance Imaging: An Official Journal of the International Society for Magnetic Resonance in Medicine 28.3 (2008): 543-558.; 2008.

Ronneberger, Olaf et al. "U-Net: Convolutional Networks for Biomedical Image Segmentation" Medical Image Computing and Computer-Assisted Intervention (MICCAI), Springer, LNCS, vol. 9351, pp. 234-241, 2015 // arXiv:1505.04597 [cs.CV].

Goldfarb James W. et al.: "Magnitude and Complex Single- and Multi-echo Water Fat Separation via End-to-End Deep Learning" in ISMRM, Nr. 5608; Jun. 1, 2018; XP040704816.

Chemical shift artifact, https://www.imaios.com/en/e-Courses/e-MRI/Image-quality-and-artifacts/chemical-shift (downloaded: Nov. 13, 2020).

Ma, Jingfei et al. "Fast Spin-Echo Triple-Echo Dixon (fTED) Technique for Efficient T2-Weighted Water and Fat Imaging" Magnetic Resonance in Medicine, vol. 58, pp. 103-109, 2007 // DOI: 10.1002/mrm.21268.

Bum Son, Jong et al.: "Deep Neural Network for Single-Point Dixon Imaging with Flexible Echo Time" in ISMRM, Nr. 4014; Apr. 26, 2019; XP040711398.

* cited by examiner

# CORRECTING THE CHEMICAL SHIFT ARTIFACTS FROM BIPOLAR DIXON MR ACQUISITION DATA

CROSS REFERENCE TO RELATED APPLICATIONS

This patent application claims priority to European Patent Application No. 21182276.2, filed Jun. 29, 2021, which is incorporated herein by reference in its entirety.

BACKGROUND

Field

The present disclosure relates to a method for correcting chemical shift artifacts (CSA) which arise in the magnetic resonance DIXON method when using bipolar readout gradients (bipolar DIXON MR) to capture the in-phase and opposed-phase echoes.

Related Art

The present disclosure lies in the field of nuclear spin tomography, also known as magnetic resonance tomography (MRT), as used in medicine for examining patients. Nuclear spin tomography is based on the use of spin echo and gradient echo sequences, which allow excellent image quality for a given measurement time.

The disclosure is applicable in particular to methods that use a binary readout gradient, for instance the magnetic resonance (MR) measurement according to the MR imaging method published by Dixon in 1984, which can be used to represent water tissue and fat tissue separately.

In his original implementation, Dixon acquired an image containing water signals and fat signals in phase, and a further image containing water signals and fat signals phase-shifted by 180°. Dixon showed that a simple summation and subtraction of the two images can yield a pure water image or a pure fat image. The DIXON method or technique essentially encodes the chemical shift difference into the signal phase with a modified data capture, and then achieves the water/fat separation through postprocessing.

The magnetic resonance method according to DIXON is generally known and is now also used in daily clinical routine. Details on performing the method according to DIXON are known, and are described, for example, in the review article of 2008 by Jingfei Ma (Jingfei Ma, "Dixon Techniques for Water and Fat Imaging", Journal of Magnetic Resonance Imaging, 28, 543-558 (2008)).

It is known, and also described by Jingfei Ma (2008), that the MR method according to DIXON results in chemical shift artifacts, which are caused by the effect of the chemical shift at the boundary layers between fat and water. Research, for instance as described in DE 10 2008 057 294 A and EP 3 796 023 A1, seeks to prevent or minimize these artifacts.

EP 3 796 023 A1 describes, for example, a method that avoids a reduction in the image quality, and thereby the occurrence of distracting artifacts, by switching over the gradient polarity between individual repetitions in the DIXON acquisition using bipolar readout gradients. This method can only be used, however, if a plurality of mean values are captured.

An MRT scan can take up to 90 minutes, which makes it impractical for some applications or patients, because it is necessary to lie still for this long time period. For instance, typically, it is not possible for babies or people suffering from Parkinson's disease or claustrophobia to remain so long in the scanner unless under general anesthetic. It is hence a fundamental objective to keep the acquisition time as low as possible while maintaining good quality.

The fast DIXON method is a measurement that is based on the DIXON method and uses a bipolar readout gradient. It is a fast spin-echo (FSE) measurement.

The fast DIXON method is known, and the implementation and advantages and disadvantages of this method are reviewed by Jingfei Ma et al. in "Fast Spin-Echo Triple-Echo Dixon (fTED) Technique for Efficient T2-Weighted Water and Fat Imaging" (Magnetic Resonance in Medicine 58; 103-109 (2007)) and by the sources cited therein.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a method in which the information obtained after an MR measurement according to the DIXON method using a bipolar readout gradient (fast DIXON) has the same or comparable quality as obtained by an MR measurement according to the DIXON method using monopolar readout gradients. The MR acquisition time shall at least not be increased in the process.

In particular, the present disclosure relates to a deep-learning-based correction method that removes the chemical shift artifacts, CSA, from the MR acquisition data.

According to one aspect, the disclosure relates to a method for correcting chemical shift artifacts, CSA, which arise in the magnetic resonance DIXON method when using bipolar readout gradients (fast DIXON MR), in particular using readout gradients in different directions (in particular different acquisition directions), to capture the in-phase and opposed-phase echoes. The method comprises the following method steps:

providing a trained CNN, which has been trained using acquisition data acquired in phase and in phase opposition by the DIXON MR method, comprising acquisition data that contains CSA in mutually opposite or different directions, and acquisition data that contains CSA in the same direction, so that the CNN is trained to transform the acquisition data obtained by the fast DIXON MR such that it exhibits, as far as possible, CSA that now arise only in the same direction;

producing control instructions for acquiring fast DIXON MR acquisition data, and in particular at least two instances of fast DIXON MR acquisition data, by acquiring the in-phase and opposed-phase echoes of the water protons and fat protons;

applying the trained CNN to the acquisition data produced in step (2) in order to minimize or remove entirely the CSA and calculate corrected acquisition data.

The technical advantage can be seen in the accelerated image-data capture and an associated significantly improved image quality, which also has a beneficial impact on the follow-up processes such as medical assessments and diagnoses.

The term "direction" relates to the readout direction. For instance, in the TSE sequence, CSA artifacts arise only in the readout direction. The readout direction of the gradients can also be understood as an acquisition direction.

The terms "in-phase" and "opposed-phase" relate to the phase relationship between water spins and fat spins. The phase relationship (i.e. in-phase or opposed-phase) can be dealt with independently of the polarity. For instance, the phase relationship has nothing to do with "monopolar" (readout gradient for in-phase and opposed-phase echo in the same direction) and "bipolar" (readout gradients in different directions). The second type is obtained by a monopolar acquisition, the first type by a bipolar acquisition.

For the purposes of training the network, in-phase and opposed-phase data from a monopolar acquisition can be sent through a Dixon algorithm as described to obtain fat images and water images. By shifting the images with respect to each other in both directions, it is possible to simulate bipolar acquisitions again, and hence training data.

The input data to the network is images containing CSA in different directions. Output data is meant to be images containing CSA in the same direction.

In an exemplary embodiment of the disclosure, step (2) is performed after (1). Alternatively, it is possible to vary the order of the steps. For instance, it can make sense to perform step (2) before step (1) by loading, for example, "old" data into the machine learning structure or the CNN.

In a further exemplary embodiment of the disclosure, the acquisitions are those in which water spins and fat spins are in phase and out of phase. The CSA arise at the boundary surfaces between water and fat. Fat and water are not acquired already separated in the acquisitions, however (although such methods do exist; they do not, however, always suppress the other species in sufficient quality, which is why the DIXON method is needed in the first place).

In a further exemplary embodiment of the disclosure, the acquisition data in step (1) and/or in particular the training data and the input data to the CNN is raw image data in k-space. Alternatively, or cumulatively, reconstructed images in image space may be involved. Alternatively, the method can also be applied in a hybrid mode, in which case the acquisition data (training data and CNN input data) is hybrid image data. "Hybrid image data" is data that is represented partly in k-space and partly in image space. Hybrid image data is in particular data for which a Fourier transform from k-space into image space has been performed only in one spatial direction, preferably the readout direction.

In a first embodiment of the disclosure, the output from the CNN can be in-phase and opposed-phase data, which can then be fed to a Dixon algorithm. It is also possible to integrate the Dixon algorithm directly into the CNN, so that the output from the CNN is directly the reconstructed image data (without CSA).

In a further exemplary embodiment of the disclosure, the CNN has a U-net architecture or a GAN architecture.

The U-net is a convolutional network architecture developed by scientists at the University of Freiburg for the purpose of fast and precise segmentation of images. In principle, successful training of deep networks requires many thousands of annotated training samples. The U-network and the associated training strategy is based on the strong use of data augmentation in order to use the available annotated input data more efficiently. The architecture consists of a contracting path to capture context and a symmetric expanding path that enables precise localization. It has been shown that such a network can be trained end-to-end from very few images and outperforms the prior best method (a sliding-window convolutional network). Moreover, the network is fast. Segmentation of a 512×512 image takes less than a second on a recent GPU. The full implementation (based on Caffe) and the trained networks are available at http://lmb.informatik.uni-freiburg.de/people/ronneber/u-net. The following publication provides technical details: http://lmb.informatik.uni-freiburg.de/Publications/2015/RFB15a. The U-net architecture has since been extended also to image reconstructions and transformations (cf. e.g. https://www.ncbi.nlm nih.gov/pmc/articles/PMC6785508/pdf/qims-09-09-1516.pdf).

The CNN architectures are usually designed to work well with balanced datasets. A problem that occurs frequently in real datasets is precisely that they are not balanced and suffer from class imbalance, and therefore, for instance, only a small number of artifact images are available for training the CNNs, whereas there are a large number of good images (without artifacts), or vice versa. This leads to the problem that, as a result of the imbalance in the data alone, the nets then tend to classify an image in a one-sided manner and according to the imbalance, because this procedure mostly led to a correct classification in the training process and hence was rewarded with a small loss. Various methods are known for reducing or correcting this imbalance. A frequently used method is data augmentation. This involves creating slightly modified copies of existing data and adding these copies to the relevant class. Another option is to adjust the weighting. In this case, mis-classifications of instances from classes containing a small amount of data are weighted more heavily.

In contrast with the approaches mentioned, generative adversarial neural networks (GANs) in this context are designed to learn the underlying data distributions from the limited images available, and then to use the learned distributions in order to generate synthetic images. GANs can be used to generate synthetic images for classes containing a small amount of image data originating from various unbalanced datasets. Thus, they could be used as an intelligent oversampling method. GANS are not just capable of generating a synthetic image but also offer a facility for changing something in the original image. GANs consist of two artificial neural nets. One net is called the generator, which generates synthetic data from a vector of latent variables. The second net is the discriminator, which assesses the data and attempts to discriminate between synthetic and real data. These two networks work "against each other" so to speak, and perform a zero-sum game in the training process. The generator attempts to generate data that is so similar to the real data that the discriminator is unable to distinguish the synthetically generated data from the real data. The first GAN architectures needed a large amount of data for the training phase and were only able to generate images of limited resolution. Newer architectures, however, such as SinGAN7 or StyleGAN28, which work with adaptive discriminator augmentation (ADA), allow high-quality images to be generated even using small datasets.

Reference is made to the following article for the use of GANs and other architectures in medicine: https://www.mdpi.com/2076-3417/10/5/1816/pdf.

In a further exemplary embodiment of the disclosure, applying the trained CNN comprises providing nxm-channel image data into an input layer of the CNN, where n is the number of readout steps, and m is the number of phase encoding steps. In particular, a 4-channel image or a 6-channel image, for example containing 256×256 pixels, can be used as the input.

In a further exemplary embodiment of the disclosure, a 3-point Dixon method can be applied. In this case, the image data is then 6-channel etc. This has advantages for the performance of the network.

In a further exemplary embodiment of the disclosure, the input data comprises real and imaginary components of the acquisition data generated from the in-phase and opposed-phase echoes, which are concatenated with each other. The terms "real/imaginary component" relate to the fact that the MR signals are complex-valued. In the processing in neural networks, these are usually split according to real and imaginary part (not magnitude and phase). In this context, "concatenated" means linking two tensors along one dimension.

Concatenating the input data is used to keep together, or to store together, data that belongs together. In the case of real image acquisitions, this might be the RGB channels, for instance.

The concatenation in the extracting branch with data from the contracting branch has the purpose of being able to restore the resolution. Otherwise, interpolating from quite a small matrix to quite a large matrix would be unstable. Therefore, the tensors of the same resolution are incorporated from the contraction branch. Usually concatenation takes place at each resolution level.

In a further exemplary embodiment of the disclosure, the training is performed with monopolar acquisition data and hence without assigning bipolar acquisition data. The learning process can be in the form of unsupervised learning. An estimation algorithm can be used to generate (estimate) bipolar in-phase and opposed-phase acquisition data from the monopolar acquisition data. In a further embodiment of the disclosure, the estimation algorithm can add noise in order to simulate acquisition data of larger bandwidth, where the bandwidth affects the position of the chemical shift.

In a further exemplary embodiment of the disclosure, the acquisition data is generated from opposed-phase echoes offset by a phase angle other than 180° by multiplying the data for the fat protons by $e^{(i*phase-angle)}$, where the phase angle is the actual dephasing in the range 0 to 2pi.

Using the magnetic resonance DIXON method that employs bipolar readout gradients, called "fast DIXON MR" or "bipolar DIXON MR" below, has the advantage over the magnetic resonance Dixon method that employs monopolar readout gradients, called "DIXON MR" or "monopolar DIXON MR" below, that the acquisition time is at least halved, and distracting motion artifacts are minimized in the acquisition. MRT examinations are often carried out on patients, and the reduction in acquisition time is a major contributing factor in the acceptance of this method.

During the acquisition of bipolar DIXON MR acquisition data, a multiplicity of k-space echoes are acquired preferably bidirectionally or in different spatial directions, with at least one echo being an in-phase (even) echo, which is captured in a first direction, and at least one echo being an opposed-phase (odd) echo, which is captured in a second direction, for instance opposite to the first direction. The k-space echo orientation is corrected between the even echo and the odd echo.

The fast DIXON MR method constitutes a two-point or multipoint method, where two-point means that one measurement is for in-phase and one measurement is for opposed-phase. This measurement can be extended to more phases, for instance to three phases, in the measurement order of opposed-phase, in-phase, opposed-phase.

The term "artifact" in the present context refers only to artifacts that are attributable to the MRT method, but not to those artifacts that arise from an incorrect choice of the various parameters. Artifacts attributable to the MRT method are, for example, motion artifacts and chemical shift artifacts (CSA).

The occurrence of said chemical shift artifacts is pronounced in an MR measurement according to the fast DIXON method, because the echoes are acquired with different polarities of the readout gradients.

A "chemical shift" refers to the property that the resonant frequency shifts slightly in proportion to the field strength according to the type of chemical bond in which a signal-emitting nucleus finds itself. As a result of their concentration in the human body, hydrogen nuclei of free water and of fat are the main contributors to the image. Their relative resonant frequency difference equals approximately 3 ppm (parts per million).

Hence the use of spin echo and gradient echo sequences leads to modulation of the signal intensities as a function of the echo time.

The CSA arises at the boundary surfaces between water and fat, and is caused by the different resonant frequencies. As a result of the slightly different frequencies of the spins of water protons and fat protons, in the MR image the positions of the differently bonded protons may be shifted with respect to each other in the direction of the readout gradient. After the Dixon reconstruction, the boundary regions in the water image are sharply delimited, and in the fat image these boundaries are blurred. For the in-phase and opposed-phase images, the artifacts as described above can be found only on the one side of the boundary surface or the other.

In the present context, quality means that the information in the associated images permits definitive statements about the acquired structures.

In the present context, in-phase means that the magnetization vectors of water (W) and of fat (F) are parallel and point in the same direction (W+F), and opposed-phase means that these magnetization vectors are parallel but point in the opposite direction (W−F).

The disclosure relates to the use of one or more neural networks, in particular a CNN (convolutional neural network), in order to alter bipolar DIXON MR acquisition data such that it corresponds to monopolar DIXON MR acquisition data and hence exhibits minimal, preferably no, CSA in different spatial directions.

The advantage of the faster acquisition time of the fast DIXON method can hence be exploited advantageously without impairing the quality of the acquisition data.

In an exemplary embodiment of the disclosure, a U-net network architecture is used. After the convolutional layers, a connection is made between a contraction path or downsampling path and an expansion path or upsampling path of the network, allowing the original data to propagate into the upsampling path.

In an alternative advantageous embodiment of the disclosure, another network architecture is used instead of the U-net, for instance a GAN (generative adversarial network).

The input layer consists of the real and imaginary parts of the in-phase and opposed-phase data of the bipolar DIXON MR acquisition in a four-channel representation. The linking or concatenation is needed in order to obtain an estimate of the un-shifted images from the two datasets (in-phase and opposed-phase) having shifts in opposite directions.

The output layer has the same dimensionality and contains in-phase and opposed-phase data having reduced or eliminated chemical shifts.

In an exemplary embodiment, since chemical shifts arise in the read-encoding direction, this dimension in image space is propagated, i.e. to use either the complete image-space representation (x,y) or a hybrid representation (x, ky). In an alternative embodiment of the disclosure, also a pure k-space representation of the data (kx, ky) can be used as the input data (both for the training and in the inference phase).

In another advantageous embodiment of the disclosure, it is also possible to use water images and fat images after the DIXON reconstruction instead of in-phase and opposed-phase images. Since these images already contain a non-linear mix of in-phase and opposed-phase images, however, the results might be worse with this approach.

In another embodiment, the input layer contains the in-phase and opposed-phase images, and the output layer contains fat images and water images and optionally a field map, which was removed from the input data, i.e. the DIXON reconstruction is incorporated in the neural net.

In order to train the net, bipolar-captured in-phase and opposed-phase data (e.g. TSE DIXON with the fast DIXON MR option) can be used as the input data, and monopolar in-phase and opposed-phase data (e.g. TSE DIXON without fast DIXON MR) can be used as the target data. An unsupervised learning method can be used. In one implementation, which is based on the PyTorch platform, a U-net can preferably be defined as the network architecture in order then to form the tensors with all the input and output data, and then to get the data divided into training and validation data, and then train the net. The net can then be trained using, for instance, backpropagation on the basis of a metric (e.g. L2 norm between desired target image and image generated by the net).

An alternative exemplary embodiment of the disclosure does not require any separately labeled data (with assigned target data) as training data, but can itself generate the training data. For example, a large number of instances of bipolar DIXON MR acquisition data can be obtained as training datasets from each instance of monopolar DIXON MR acquisition data. The algorithm can provide an assignment as to which of the images reconstructed from the Dixon algorithm contains fat or water respectively.

First, a plurality of chemical shifts are simulated by applying in the readout direction different (sub-)pixel shifts, each of different signs, to fat images. The technical background of this is to simulate the bipolar readout of each acquisition.

Second, a field map is either extracted from the conventional DIXON reconstruction or a corresponding pre-scan, or synthesized from the images.

A multiplicity of field maps are generated from this field map, for instance by adding offsets, multiplying by scalars or superimposing an eigenfunction, in particular a spherical harmonic.

The fat images are then added to the water image and subtracted from the water image with subsequent multiplication by the complex exponential of the synthesized or synthetic field maps, in order to generate synthesized or synthetic bipolar acquisition data.

Moreover, all the resultant images can be multiplied further by additional phase maps. In addition, synthetic noise can be injected in order to simulate acquisition data of greater bandwidth.

Furthermore, phase-offset data having a phase angle other than 180° can be generated for the opposed-phase case by multiplying the fat data by e^(i*phase−angle), where the angle is the actual dephasing in the range of 0 to 2pi.

Target images for the training are obtained by proceeding as described, but 1. omitting the step of pixel shifting, 2. injecting less noise, and 3. omitting eddy-current-induced effects on the field map.

The latter could be performed by subtracting a field map obtained using conventional approaches (i.e. a 2-echo or 3-echo gradient echo acquisition) from the field map obtained using the DIXON algorithm on a bipolar dataset.

In an exemplary embodiment, the phase offset (dephasing) equals 180°. In this case, the vectors are exactly opposite and the signals cancel each other out. Alternative embodiments provide a phase offset that differs from 180°. The network must then be trained accordingly with data having this phase offset.

Features, advantages or alternative embodiments described above regarding the inventive method can also be applied equally to the other claimed subject matter, and vice versa. In other words, the physical claims (which relate to a system or a computer program product, for example) can also be developed by combining with features described or claimed in connection with the method. The corresponding functional features of the method are embodied in this case by corresponding physical modules, in particular by hardware modules or microprocessor modules, of the system or product, and vice versa.

According to a further aspect, the disclosure relates to a processing unit for a magnetic resonance imaging device. The processing unit is designed to implement the method as described above. The processing unit comprises:

a memory or an interface to the memory, in which is stored a trained CNN that has been trained with acquisition data acquired in phase and in phase opposition by the DIXON method, comprising: acquisition data that exhibits CSA in the same direction, and acquisition data that contains CSA in mutually opposite directions, so that the CNN is trained to transform the acquisition data calculated by the bipolar DIXON MR such that it exhibits, as far as possible, CSA that now arise only in the same direction;

wherein the magnetic resonance imaging device is intended to produce bipolar DIXON MR acquisitions by acquiring the in-phase and opposed-phase echoes of the water protons and fat protons;

wherein the processing unit is intended to apply the trained CNN to the acquisition data produced in step (2) of the method according to the disclosure in order to minimize or remove entirely the CSA and calculate the corrected data or images.

The object is also achieved by a computer program product comprising computer program code for performing all the method steps of the above-detailed method when the computer program is executed on a computer. It is also possible that a computer program may be stored on a medium that can be read by a computer, that when executed, preforms the method according to exemplary embodiments.

Figure 1:
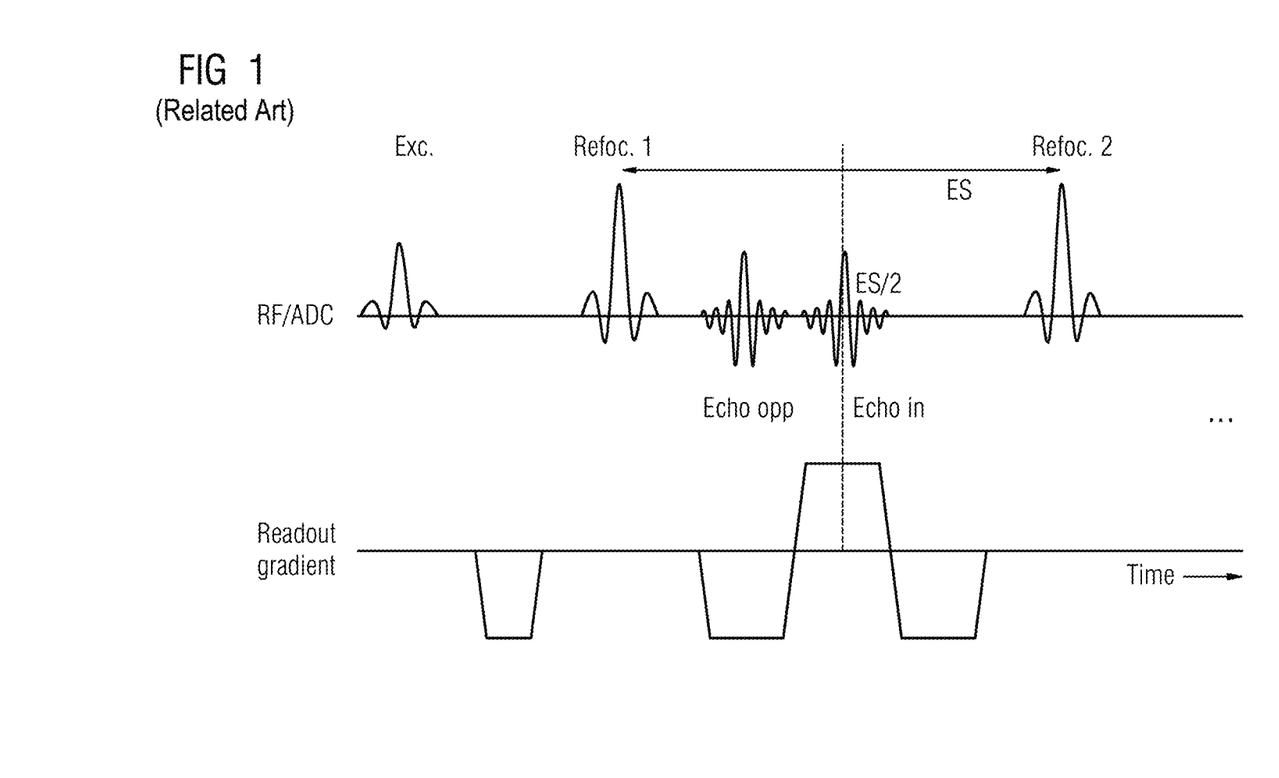
FIG. 1 shows a sequence diagram for a conventional bipolar TSE Dixon (fast DIXON) acquisition.

FIG. 1 shows a typical sequence diagram of a conventional fast Dixon acquisition. In Dixon imaging, the data capture takes place at at least two different time instants so that the signal from water spins and fat spins is in phase or out of phase (opposed phase). A post-processing algorithm can then separate the fat and water signals and generate two images showing just the fat or water component. In-phase and opposed-phase echoes are often acquired in a bipolar manner in order to accelerate the capture. This is performed, for example, in VIBE imaging and with the fast DIXON function for TSE, in which the capture of an in-phase echo and an opposed-phase echo takes place after a refocusing pulse (labeled "Refoc" in FIG. 1). The interval between an in-phase and out-of-phase state decreases linearly with increasing field strength. At 3 T, this interval is only about 1.2 ms. A bipolar gradient is used to read out in-phase and opposed-phase echoes. Since the position of the chemical shift artifacts depends on the polarity of the gradient (cf. FIG. 2), the artifacts for the opposed-phase and in-phase echoes arise at different spatial positions. (FIG. 1 shows only the first part of the echo chain).

For conventional monopolar DIXON it holds that:

$IP=W(\delta)+F(\delta+chs)$, where IP denotes in-phase, and W stands for water and F for fat;

$OP=W(\delta)-F(\delta+chs)$, where OP denotes opposed phase.

For bipolar DIXON it holds that:

$$IP=W(\delta)+F(\delta+chs)$$

$$OP=W(\delta)-F(\delta-chs)$$

where IP and OP are the in-phase and opposed-phase datasets, W is the water signal, F is the fat signal, $\delta$ is the voxel position, and chs is the chemical shift introduced by the difference between the Larmor frequencies of water protons and fat protons.

The fat images and water images for the conventional DIXON imaging can be obtained by adding and subtracting in-phase and opposed-phase images:

$$0.5*(IP+OP)=W(\delta)$$

$$0.5*(IP-OP)=F(\delta+chs)$$

In this case, the chemical shift appears only in the fat image, as a global shift for all the voxels. Fat images and water images can then be aligned, if required, by simple spatial registration.

Figure 2:
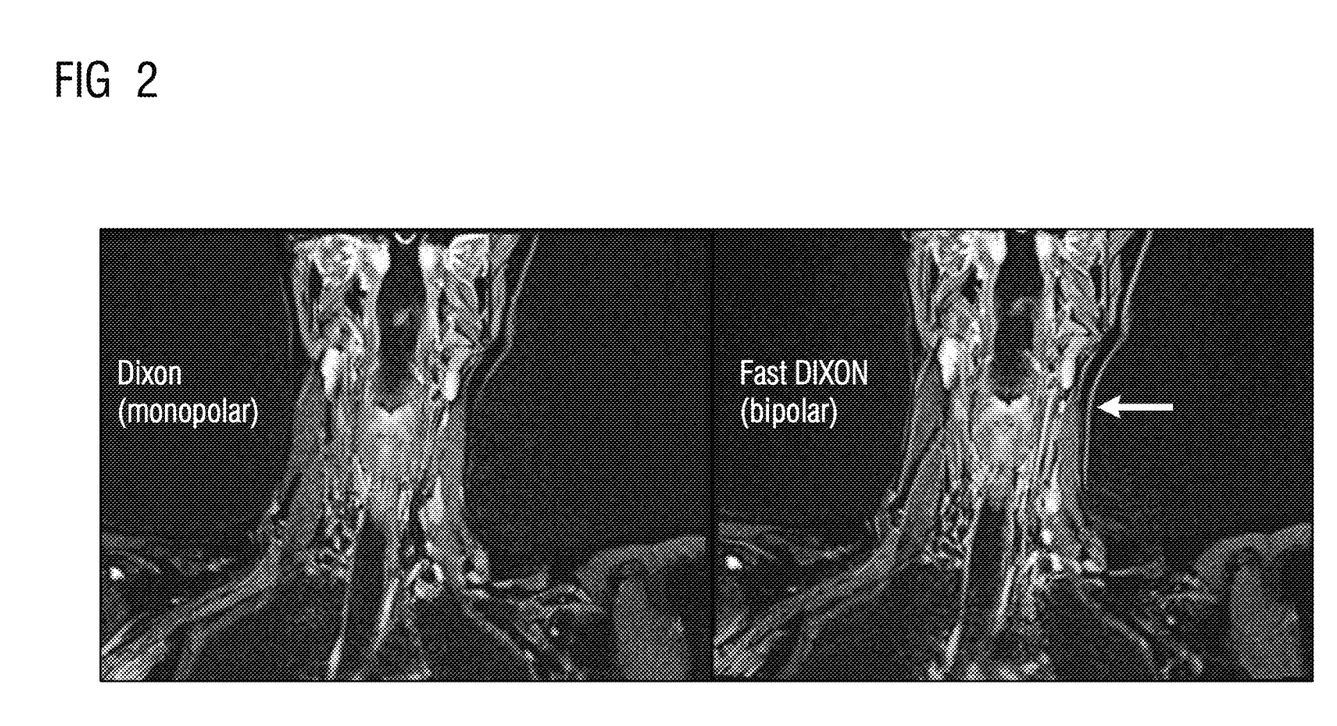
FIG. 2 shows examples of a monopolar DIXON MR acquisition and of a bipolar fast DIXON MR acquisition according to an exemplary embodiment.

FIG. 2 shows in an example the quality differences for a monopolar and bipolar Dixon acquisition. The chemical shift artifact, CSA, is caused by different Larmor frequencies for fat protons and water protons and can be seen in the acquisitions as a line artifact. If the readout gradient increases from left to right, fat is shifted to the left; if the readout gradient decreases from left to right, fat is shifted to the right. On the right-hand side is shown the effect of the different chemical shift on the final fat images and water images. Ringing artifacts appear at the fat/water boundaries in particular in the water images. (Source: Leinhard et al, ISMRM 2008).

Figure 3:
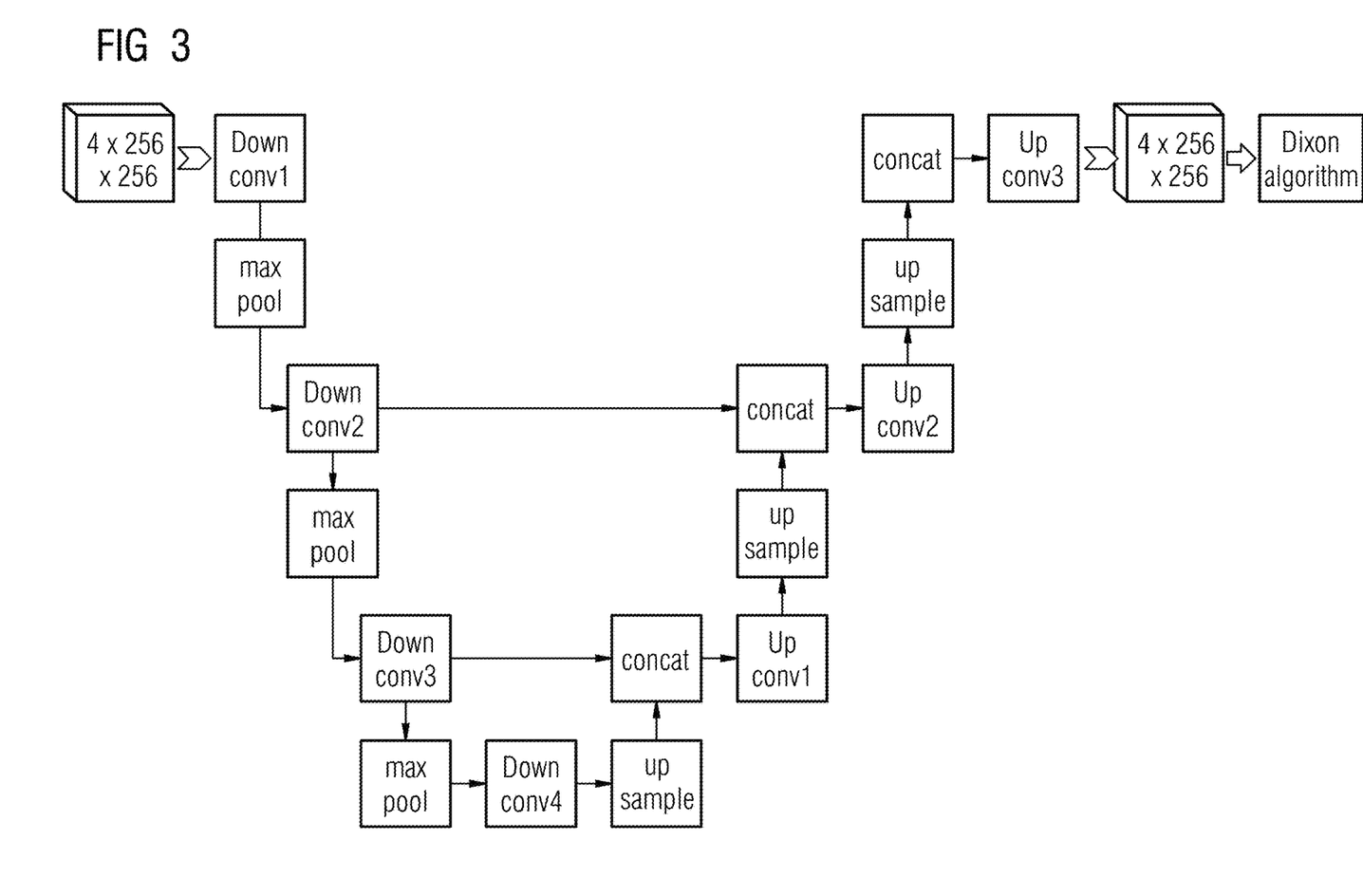
FIG. 3 shows a block diagram of a U-net architecture according to an exemplary embodiment for correcting CSA that are prominent in fast DIXON methods that use bipolar readout gradients to capture the in-phase and opposed-phase echoes.

FIG. 3 shows a possible network architecture. A U-net architecture with skip connections is selected here, which allows the original data to propagate into the upsampling path of the network.

The input and output data consists of real and imaginary parts of in-phase and opposed-phase data, which can be concatenated in the channel dimension and yield a 4-channel image. A CNN architecture known from the prior art can be used, as developed by Ronneberger et al (cf. Ronneberger, Olaf; Fischer, Philipp; Brox, Thomas (2015). "U-Net: Convolutional Networks for Biomedical Image Segmentation". arXiv:1505.04597). After the upsampling, the 4-channel data is divided into in-phase and opposed-phase images and fed into a conventional Dixon algorithm in order to obtain fat images and water images in a final step.

The input layer consists of the real and imaginary parts of the in-phase and opposed-phase data of the bipolar Dixon acquisitions in a 4-channel representation. The concatenation is needed in order to facilitate the estimate of the un-shifted images from the two datasets having shifts in opposite directions.

Instead of a U-net, other network architectures could also be used, for instance a generative adversarial network (GAN).

Figure 4:
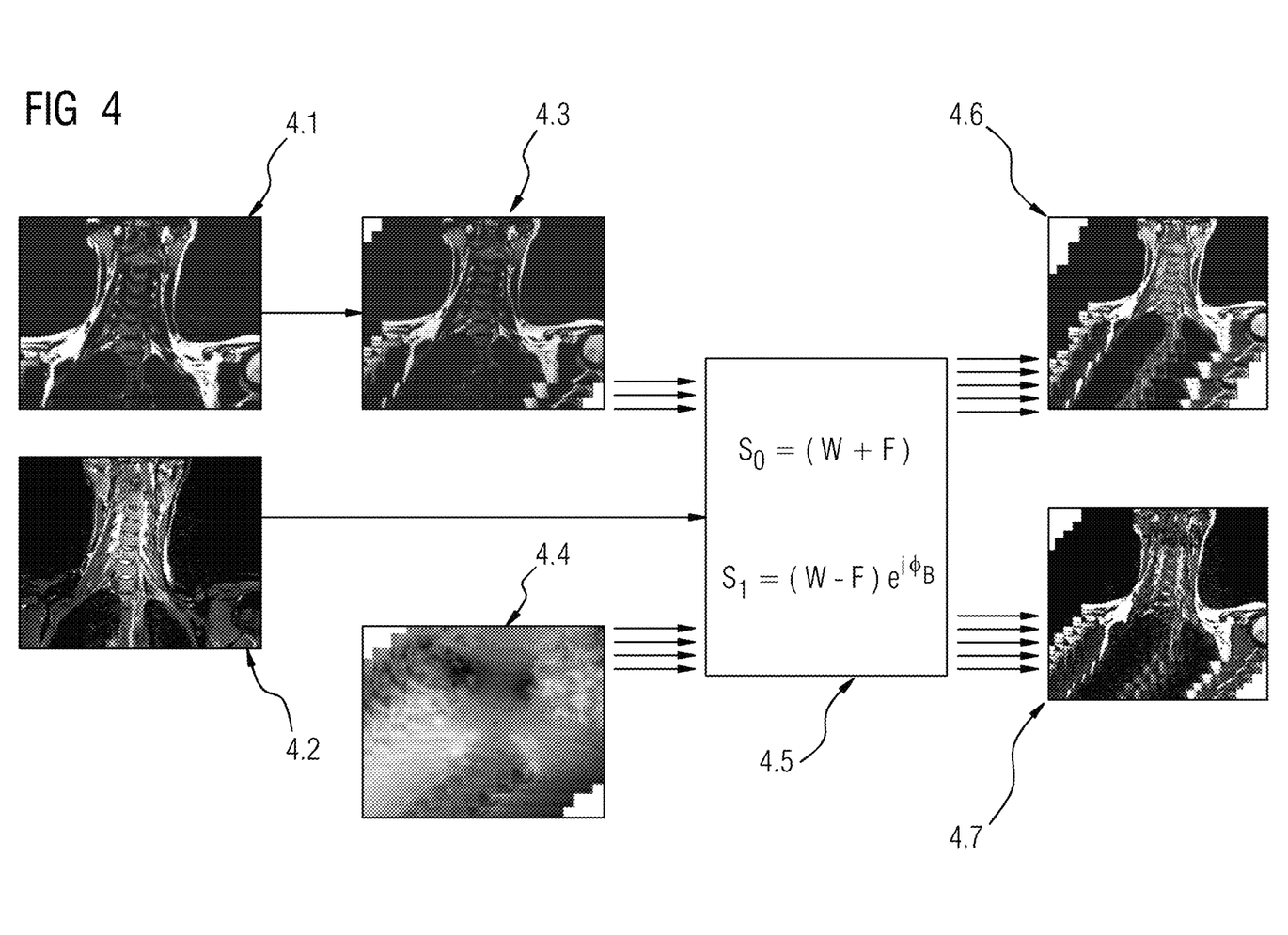
FIG. 4 shows an overview diagram of a training of the network according to an exemplary embodiment.

FIG. 4 uses example images to show a training approach to training the network that allows a multiplicity of training datasets to be produced from a single monopolar Dixon reconstruction.

The reference sign 4.1 labels the monopolar fat acquisition (fat image data), and 4.2 labels the monopolar water acquisition (water image data). The reference sign 4.3 represents applying a multiplicity of pixel shifts along the readout direction to simulate the CSA of different bandwidths. Reference sign 4.4 labels the use of the field map ΦB from the Dixon reconstruction. Optionally, various other modified field maps can be generated. In 4.5, a multiplicity of synthetic in-phase and opposed-phase images are generated according to the equation shown in FIG. 4. Simulated bipolar in-phase images, shown in 4.6, and the simulated bipolar opposed-phase images, shown in 4.7, can then be generated therefrom.

The proposed method allows fast capture of bipolar Dixon data with improved image quality, because the chemical shift in different directions is removed before the Dixon reconstruction, resulting in less blurring. There is also a reduction in ringing artifacts (resulting from the Fourier-transform-based image processing calculations of a sampled signal row).

In addition to Dixon imaging, the method can also be employed for other bipolar capture schemes such as mapping sequences or TGSE sequences.

Figure 5:
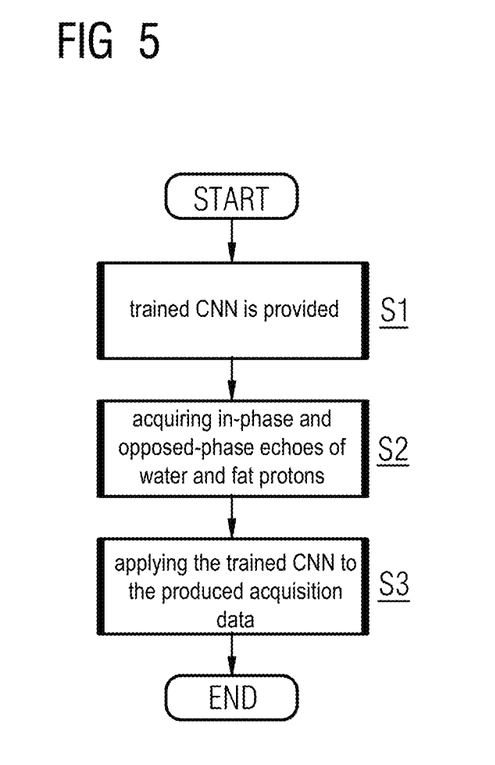
FIG. 5 shows a flowchart of a method according to an exemplary embodiment.

FIG. 5 shows a flow diagram of the method according to an exemplary embodiment of the disclosure. After start, the trained CNN is provided in step S1. The network may have been trained in preprocessing. For this purpose, training data can have been generated synthetically, for instance by using image processing procedures to generate some of the images, for instance the images containing CSA in different directions, from existing image data. In step S2, at least two bipolar Dixon acquisitions are produced by acquiring the in-phase and opposed-phase echoes of the water protons and fat protons. In step S3, the trained CNN is applied to the acquisition data produced in step S2 in order to minimize or remove entirely the CSA and calculate corrected acquisition data.

Figure 6:
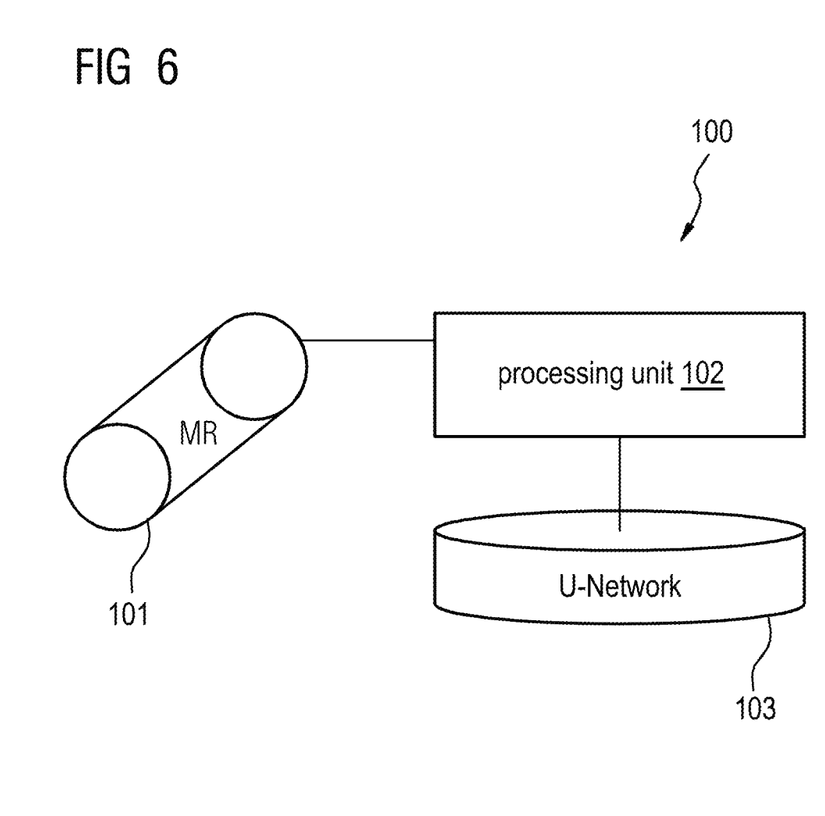
FIG. 6 shows a block diagram of a magnetic resonance imaging device according to an exemplary embodiment.

FIG. 6 is a block diagram of a system 100 for reconstructing MR acquisitions with correction of the CSA. The MR scanner or the magnetic resonance imaging device 101 is used to capture bipolar Dixon MR acquisitions, and is connected via a data interface to a processing unit 102, which may be in the form of a reconstruction computer. The reconstruction computer 102 is additionally connected via a network connection to a memory 103, in which is stored the trained CNN, in particular a U-net as described in detail above. In an exemplary embodiment, the processing unit 102 includes processing circuitry that is configured to perform one or more respective functions and/or operations of the processing unit 102. For example, the processing unit 102 may include one or more processors. The processing unit 102 may include one or more memory units and/or may be configured to access one or more external memory units.

In conclusion, it should be noted that, as a basic principle, the description of the disclosure, and the exemplary embodiments, shall not be considered restrictive as regards a specific physical realization of the disclosure. All the features illustrated and explained in association with the individual embodiments can be provided in various combinations in the subject matter according to the disclosure to achieve the advantageous effects of these embodiments simultaneously.

The scope of protection of the present disclosure is defined by the claims below and is not restricted by the features explained in the description or illustrated in the figures.

In particular it is obvious to a person skilled in the art that the disclosure can be applied not just to specific MR devices from one manufacturer but also to other MR devices from other manufacturers. In addition, the components of the magnetic resonance imaging device can be distributed over a plurality of physical products. For instance, in particular the memory and/or the processing unit can be relocated to a separate or additional electronic module.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for correcting chemical shift artifacts (CSA) arising in a DIXON magnetic resonance (MR) method when using bipolar readout gradients (fast DIXON MR) to capture in-phase and opposed-phase echoes, the method comprising:
   providing a trained convolutional neural network (CNN), which has been trained using acquisition data acquired in phase and in opposed phase by the DIXON MR method, comprising acquisition data that contains CSA in mutually opposite directions, and acquisition data that contains CSA only in one direction, so that the CNN is trained to transform acquisition data obtained by the fast DIXON MR method such that the acquisition data acquired by the fast DIXON MR method exhibits CSA that arise only in the same direction;
   acquiring fast DIXON MR acquisition data using respective control instructions; and
   applying the trained CNN to the acquisition data acquired using the respective control instructions to minimize or entirely remove the CSA and to calculate corrected acquisition data.

2. The method as claimed in claim 1, wherein the respective control instructions are for acquiring at least two instances of the fast DIXON MR acquisition data.

3. The method as claimed in claim 2, wherein the at least two instances of the fast DIXON MR acquisition data are acquired by acquiring the in-phase and opposed-phase echoes of water protons and fat protons.

4. The method as claimed in claim 1, wherein the fast DIXON MR acquisition data is acquired before the trained CNN is provided.

5. The method as claimed in claim 1, wherein the acquired acquisition data is acquisition data acquired when water spins and fat spins are in phase and in opposed phase, and in which the CSA are present in the acquisition data at the boundary surfaces between water and fat.

6. The method as claimed in claim 1, wherein the acquisition data used to train the CNN is raw image data in k-space, reconstructed images in image space, or hybrid image data.

7. The method as claimed in claim 1, wherein the CNN has a U-net architecture or a generative adversarial network (GAN) architecture.

8. The method as claimed in claim 1, wherein applying the trained CNN comprises providing 4-channel or 6-channel image data into an input layer of the CNN.

9. The method as claimed in claim 1, wherein input data to the CNN comprises real and imaginary components of the acquisition data generated from the in-phase and opposed-phase echoes, which are concatenated with each other.

10. The method as claimed in claim 1, wherein the training is performed with monopolar acquisition data without assigning bipolar acquisition data, wherein an estimation algorithm is used to generate bipolar in-phase and opposed-phase acquisition data from the monopolar acquisition data.

11. The method as claimed in claim 10, in which the estimation algorithm adds noise to simulate acquisition data having a lower signal-to-noise ratio.

12. The method as claimed in claim 10, wherein the acquired acquisition data is generated from opposed-phase echoes offset by a phase angle other than 180° by multiplying the data for the fat protons $e^{(i \times phase-angle)}$, where phase angle is the actual dephasing in the range 0 to $2\pi$.

13. A non-transitory computer program product having a computer program which is directly loadable into a memory of a controller of a magnetic resonance device, when executed by the controller, causes the magnetic resonance device to perform the method as claimed in claim 1.

14. A non-transitory computer-readable storage medium with an executable program stored thereon, that when executed, instructs a processor to perform the method of claim 1.

15. A processing unit for a magnetic resonance (MR) imaging device, comprising:
   a memory storing a trained convolutional neural network (CNN) that has been trained with acquisition data acquired in phase and in opposed phase by a DIXON MR method, the acquisition data including: acquisition data that contains chemical shift artifacts (CSAs) in mutually opposite directions, and acquisition data that contains CSA only in one direction, so that the CNN is trained to transform the acquisition data obtained by a DIXON MR method using bipolar readout gradients (fast DIXON MR) such that the acquisition data acquired with the fast DIXON MR method exhibits CSA that arise only in the same direction, wherein the MR imaging device is configured to produce bipolar DIXON MR acquisitions by acquiring the in-phase and opposed-phase echoes of the water protons and fat protons; and
   processing circuitry configured to apply the trained CNN to the acquisition data acquired with the fast DIXON MR method to minimize or entirely remove the CSA and to calculate the corrected acquisition data.

* * * * *